(12) United States Patent
Star et al.

(10) Patent No.: US 6,790,636 B1
(45) Date of Patent: Sep. 14, 2004

(54) RAPID FLUORESCENT LABELING OF TISSUE FOR MICRODISSECTION USING FLUORESCENT SPECIFIC BINDING AGENTS

(75) Inventors: Robert A. Star, Bethesda, MD (US); Hiroshi Murakami, Miyagi (JP); Lance A. Liotta, Bethesda, MD (US); Kenneth R. Spring, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 25 days.

(21) Appl. No.: 09/881,446

(22) Filed: Jun. 13, 2001

Related U.S. Application Data

(60) Provisional application No. 60/211,698, filed on Jun. 14, 2000.

(51) Int. Cl.$^7$ .......................... G01N 33/48; G01N 33/53
(52) U.S. Cl. .................... 435/40.5; 435/7.1; 435/40.52; 436/164; 436/172
(58) Field of Search ................................ 435/7.1, 40.5, 435/40.52; 436/164, 172

(56) References Cited

U.S. PATENT DOCUMENTS

| | | | |
|---|---|---|---|
| 4,922,092 | A | 5/1990 | Rushbrooke et al. |
| 5,742,115 | A | 4/1998 | Gertsenshteyn |
| 5,843,657 | A | 12/1998 | Liotta et al. |
| 6,040,657 | A | 3/2000 | Vrescak et al. |
| 6,251,467 | B1 * | 6/2001 | Liotta et al. ................ 427/2.11 |

FOREIGN PATENT DOCUMENTS

| | | |
|---|---|---|
| WO | WO 98/35216 | 8/1998 |
| WO | WO 00/05587 | 2/2000 |

OTHER PUBLICATIONS

Taylor et al. (Immunohistochemistry: Principles and Practice, American Society for Microbiology, 1996, pp. 369–379).*
Fend et al., "Immuno–LCM: Laser Capture Microdissection of Immunostained Frozen Sections for mRNA Analysis," *Am. J. Pathol.* 154(1):61–66, Jan. 1999.
Goldsworthy et al., "Effects of Fixation on RNA Extraction and Amplication from Laser Capture Microdissected Tissue," *Mol. Carcin.* 25:86–91, 1999.
Kohda et al., "Analysis of segmental renal gene expression by laser capture microdissection," *Kidney Int.* 57:321–331, 2000.
Darling et al., "Revertant mosaicism: partial correction of a germ–line mutation in COL17A1 by a frame–restoring mutation," *J. Clin. Invest.* 103(10):1371–1377, May 1999.
Emmert–Buck et al., "Laser Capture Microdissection," *Science* 274(5289):998–1001, Nov. 8, 1996.
Fink et al., "Immunostaining and Laser–Assisted Cell Picking for mRNA Analysis," *Lab Invest.* 80(3):327–333, Mar. 2000.
Jin et al., "Analysis of Anterior Pituitary Hormone mRNA Expression in Immunophenotypically Characterized Single Cells after Laser Capture Microdissection," *Lab Invest.* 79(4):511, Apr. 1999.

* cited by examiner

*Primary Examiner*—Long V. Le
*Assistant Examiner*—Gary W. Counts
(74) *Attorney, Agent, or Firm*—Klarquist Sparkman LLP

(57) ABSTRACT

Methods are disclosed for rapid and specific fluorescent staining of biological tissue samples that substantially preserve biological molecules such as mRNA. Methods for microdissecting tissue to obtain pure populations of cells or tissue structures based upon identifying and excising cells or tissue structures that are labeled with fluorescent specific binding agents are also included. A laser capture microdissection apparatus useful for identifying and isolating cells and tissue structures following rapid immunofluorescent staining is also disclosed.

3 Claims, 8 Drawing Sheets

——— WHITE LIGHT ILLUMINATION PATH
——— LASER BEAM PATH

RAPID FLUORESCENT LABELING OF TISSUE FOR MICRODISSECTION USING FLUORESCENT SPECIFIC BINDING AGENTS

CROSS REFERENCE TO RELATED APPLICATIONS

This application claims the benefit of U.S. Provisional Application No. 60/211,698, filed Jun. 14, 2000. The provisional application is incorporated herein in its entirety.

FIELD OF THE DISCLOSURE

The disclosure relates to methods for rapidly identifying and isolating cells and tissue structures in a manner that preserves biological molecules.

BACKGROUND

Laser Capture Microdissection (LCM) is a recently developed method that enables researchers to conveniently perform microscopic dissections of biological tissue samples and obtain pure populations of defined tissue structures and cells (see for example, Emmert-Buck et al., *Science*, 274: 998–1001, 1996). LCM combines direct microscopic visualization and a rapid one-step isolation of selected cell populations from tissue sections. In the method, a transparent thermoplastic film (the capture film) is placed over the surface of a tissue section and irradiated with laser pulses that thermally fuse the film to the tissue section. By viewing the tissue section through a microscope, a researcher can direct the laser pulses onto specific portions of the tissue section and "capture" desired cells or tissue structures. Because of the small diameter of the focussed laser beam, small cell clusters or even single cells may be captured. When the overlying film is lifted from the tissue section, the specific portions of tissue that were fused to the film are excised from the tissue section, leaving behind unselected, surrounding tissue. The excised tissue portions may then be removed from the film and utilized, for example, in studies of cell-specific gene expression. The LCM process is shown schematically in FIG. 1. LCM is especially useful for isolating structures from injured or fibrotic tissue, since manual dissection under these conditions is impossible.

The principal difficulty associated with isolating cells and tissue structures by LCM and other microdissection techniques, however, lies in identification of specific types of cells and specific types of structure within a tissue sample. Cell morphology and histochemical staining methods are adequate to identify cells in certain tissue types, but in heterogeneous tissues, such as those found in the kidney and in many tumors, cells and tissue structures may be morphologically and histochemically indistinguishable. Visual differentiation of cells or tissue structures is especially difficult when tissue samples are prepared as frozen sections and viewed through the capture film.

Immunohistochemical staining is another method for identifying individual cell types and tissue structures within a tissue section that distinguishes cells according to their production of specific antigens (i.e., according to their immunophenotype). Such staining allows morphologically similar but functionally different cells to be differentiated. Unfortunately, immunohistochemical staining regimens typically foster loss of biological molecules, such as mRNA. For example, Jin et al. (Jin et al., *Lab. Invest.*, 79: 511–513, 1999) noted a lower yield of reverse-transcription polymerase chain reaction (RT-PCR) products (i.e., a lower initial mRNA concentration) from tissue samples that were immunohistochemically stained in a conventional manner.

Fend et al. (Fend et al., *American Journal of Pathology*, 154: 61–66, 1999) developed a rapid immunohistochemical method in which the total time tissue is exposed to aqueous solutions is about 8 minutes. Nonetheless, despite the rapid staining protocol, much mRNA is lost. For example, 99% of the β-actin mRNA from LCM isolated nephron segments is lost with this staining technique (Kohda et al., *Kidney International*, 57: 321–331, 2000).

Fink et al. (Fink et al., *Lab. Invest.*, 80: 327–333, 2000) describe immunohistochemical and immunofluorescence methods for identifying cells for laser-assisted microdissection (a technique where a laser beam is used to cut selected portions from a tissue section). The study examined the influence of fixation method, antibodies and staining reagents, incubation and total processing times and digestion with proteinase K on mRNA recovery from microdissected tissue samples. Fink et al. disclose an immunofluorescence method that includes as little as six minutes of exposure of a tissue section to aqueous antibody solutions. Moreover, their results indicated that antibodies themselves contribute to loss of mRNA, and they suggest reducing the number of antibodies as part of an immunofluorescence staining regimen designed to preserve mRNA in microdissected tissue samples. Furthermore, they note that their method for combined immunofluorescent staining and laser-assisted microdissection requires an inconvenient shift from fluorescence imaging to brightfield imaging to perform the actual dissection.

What is needed is a more convenient microdissection method that permits identification of particular cell types and tissue structures through specific binding interactions, such as immunochemical interactions, yet which better preserves biological molecules. A method that preserves mRNA and yet allows identification and dissection of tissues according to their specific binding interactions with other molecules is especially needed to study gene expression at the individual cell or tissue structure level.

SUMMARY

The disclosure provides methods for microdissecting tissue, or preparing tissue for microdissection, by labeling a sample of the tissue by exposing the tissue to a sufficient concentration of a labeled specific binding agent for a sufficiently short period of time to reduce a binding time of the agent to the tissue. These methods allow reduction in the loss of a biomolecule (such as mRNA) in the tissue, while allowing a component of interest in the sample to be detected by a labeled specific binding agent Alternatively, a solvent for the specific binding agent can be selected which avoids or diminishes loss of the biomolecule of interest from the tissue. For example, a non-aqueous solvent could be used, optionally in combination with the reduced binding time.

In particular embodiments the labeled specific binding agent is a fluorescent specific binding agent, and the component of interest in the sample is identified by detecting fluorescence in the tissue, for example fluorescence of a sub-population of cells. Once these components have been identified, they may be microdissected and isolated from other components of the tissue. This approach allows certain subsets of microscopic structures (such as cells that express surface antigens, for example antigens associated with disease) to be microdissected from the tissue, and compared to cells that are not labeled. The preservation of biomolecules in the tissue enhances molecular analysis of the component of interest, for example by permitting more accurate levels of mRNA in the dissected cells to be determined, as a measure of differential gene expression.

Mere mention of an aspect of a method, composition, or device in this Summary is not intended to imply that it is an essential aspect of the invention.

DETAILED DESCRIPTION OF THE DISCLOSURE

Figure 1A:
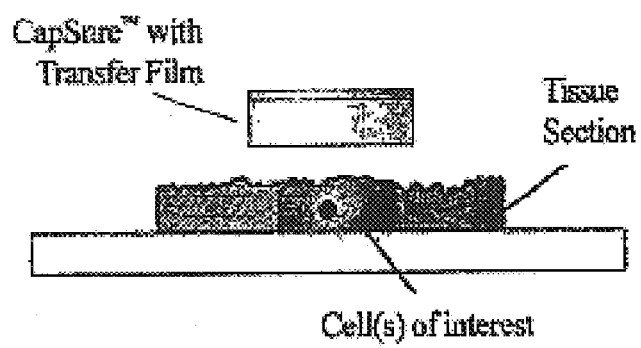
FIG. 1A illustrates that a transparent thermoplastic film is placed on top of a tissue section.
Figure 1B:
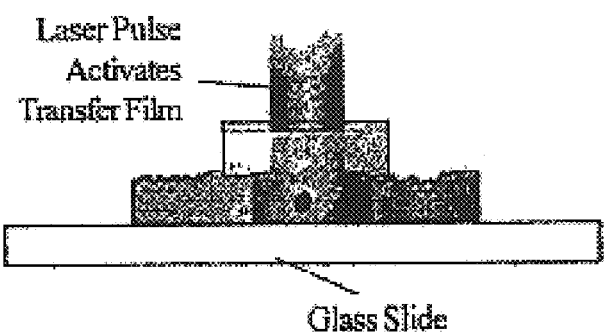
In FIG. 1B, a laser beam activates the transfer film, causing the film to melt and fuse to the selected cells. The selected cells adhere to the film, and can be lifted away from the sample as shown in FIG. 1C. See, for instance, Emmert-Buck et al., Science 274:998–1001, 1996.
Figure 1C:
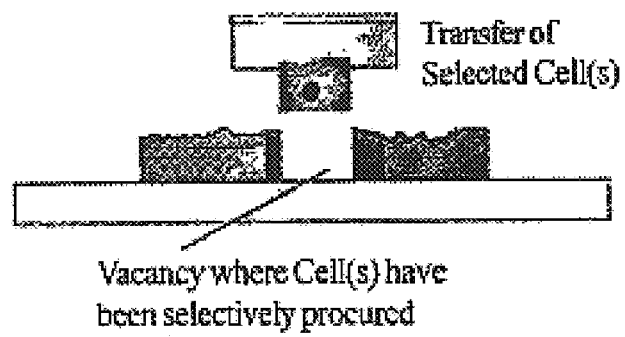
FIG. 1 is a schematic drawing illustrating an example of laser capture microdissection.

The disclosure provides methods for microdissecting tissue, or preparing tissue for microdissection, by labeling a sample of the tissue by exposing the tissue to a sufficient concentration of a labeled specific binding agent for a sufficiently short period of time to reduce a binding time of the agent to the tissue. These methods allow reduction in the loss of a biomolecule (such as mRNA) in the tissue, while allowing a component of interest in the sample to be detected by a labeled specific binding agent. Alternatively, a solvent for the specific binding agent can be selected which avoids or diminishes loss of the biomolecule of interest from the tissue. For example, a non-aqueous solvent could be used, optionally in combination with the reduced binding time.

In particular embodiments the labeled specific binding agent is a fluorescent specific binding agent, and the component of interest in the sample is identified by detecting fluorescence in the tissue, for example fluorescence of a sub-population of cells. Once these components have been identified, they may be microdissected and isolated from other components of the tissue. This approach allows certain subsets of microscopic structures (such as cells that express surface antigens, for example antigens associated with disease) to be microdissected from the tissue, and compared to cells that are not labeled. The preservation of biomolecules in the tissue enhances molecular analysis of the component of interest, for example by permitting more accurate levels of mRNA in the dissected cells to be determined, as a measure of differential gene expression.

In some embodiments a signal from the fluorescent specific binding agent is intensified (for example optically, digitally or electronically intensified) to provide an intensified image signal that is used to identify the component of interest. The intensified image is particularly useful in embodiments in which a relatively low concentration of specific binding agent is used. In other embodiments tissue components are microdissected with a laser beam, and the image of the laser beam is selectively filtered to reduce laser-induced distortion of the intensified image, such as enlargement of the image of a tracking beam. For example, the heat radiated by the tracking beam may be filtered out of the image to eliminate undesired "blooming" of the tracking beam, or selective filters may be used that only identify particular wavelengths of light.

In particular embodiments the specific binding agent comprises an aqueous solution, and the biomolecule is RNA, DNA or a protein, which is reduced or at least partially eliminated (for example by degradation or physical loss) in the presence of water. In more particular embodiments, microdissecting comprises applying a capture member to the sample of tissue, and applying laser energy to the capture member above the component of interest to adhere the component to the capture member. The capture member is then removed from the tissue sample, with the target cells removed.

In particular embodiments, the sufficient concentration of fluorescent specific binding agent is sufficient to avoid loss of more than about 5% of the biomolecule, for example more than about 10, 20, 30, 40, 50, 60, 70, 80, 90 or 95% of the biomolecule (such as mRNA). Substantial preservation of the biomolecule permits more accurate assessment of the normal cellular presence of the biomolecule, for example better quantitation of mRNA levels.

Also included in the disclosure is an apparatus for rapid immunofluorescence laser capture microdissection, comprising a laser capture microdissection microscope, a light source capable of exciting fluorescence from fluorescent specific binding agents disposed to illuminate a sample placed on the sample stage of the microscope, an image intensifier disposed between the sample stage of the microscope and an image acquisition system, and an infrared filter disposed between the sample stage and the image intensifier.

The illustrative embodiments that follow may be better understood by first understanding terms in the art that are relevant. The following explanations and methods are provided to better define the present disclosure and to guide those of ordinary skill in the art in the practice of this disclosure. Definitions of common terms may also be found in Rieger et al., *Glossary of Genetics: Classical and Molecular*, 5th edition, Springer-Verlag: New York, 1991. Additional definitions of terms commonly used in molecular genetics can be found in Benjamin Lewin, *Genes V* published by Oxford University Press, 1994 (ISBN 0-19-854287-9); Kendrew et al (eds.), The *Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Abbreviations and Explanations of Terms

DEPC—diethylpyrocarbonate
LCM—laser capture microdissection
IF—immunofluorescence
IF-LCM—immunofluorescence laser capture microdissection
THP—Tamm-Horsfall Protein
AQP-2—aquaporin-2
TAL—thick ascending limb (a structure in kidney tissue)
H&E—hematoxylin-eosin (a histochemical stain)
BAT(rBAT)—basic amino acid transporter
mRNA—messenger RNA
RNA—ribonucleic acid
DNA—deoxyribonucleic acid
MDH—malate dehydrogenase
PBS—phosphate buffered saline
TBS—Tris-buffered saline
H&E—hematoxylin and eosin
CCD—charge coupled device The singular forms "a," "an," and "the" refer to one or more than one, unless the context clearly dictates otherwise.

Antibodies—The term antibodies encompasses monoclonal and polyclonal antibodies that are specific for a particular antigen, i.e., which bind substantially only to the antigen when assessed using the methods described below, as well as immunologically effective portions ("fragments") thereof. Antibodies used in the present disclosure may be monoclonal antibodies (or immunologically effective portions thereof) and may also be humanized monoclonal antibodies (or immunologically effective portions thereof). Immunologically effective portions of monoclonal antibodies include Fab, Fab', F(ab')$_2$ Fabc and Fv portions (for a review, see Better and Horowitz, 1989). Antibodies may also be produced using standard procedures described in a number of texts, including *Antibodies, A Laboratory Manual* by Harlow and Lane, Cold Spring Harbor Laboratory (1988).

The determination that a particular agent binds substantially only to a particular antigen may readily be made by using or adapting routine procedures. One suitable in vitro assay makes use of the Western blotting procedure (described in many standard texts, including *Antibodies, A Laboratory Manual* by Harlow and Lane). Western blotting may be used to determine that a given antigen binding agent, such as an anti-Tamm Horsfall protein monoclonal antibody, binds substantially only the given antigen, such as the Tamm-Horsfall protein.

Antigen—a molecule, fragment thereof, or a conjugate of the molecule or fragment with another molecule that elicits an immune response in an animal host, including but not limited to mice, rats, humans, sheep, pigs, and goats.

cDNA (complementary DNA)—A piece of DNA lacking internal, non-coding segments (introns) and regulatory sequences that determine transcription. cDNA is synthesized in the laboratory by reverse transcription from messenger RNA extracted from cells.

Fluorescent Specific Binding Agent—fluorescent specific binding agents are fluorescent (intrinsically or after conjugation with a fluorescent moiety) molecules that preferentially bind in a specific manner to other molecules that are present inside or on the surface of particular types of cells or tissue structures. The term fluorescent specific binding agent includes fluorescently labeled primary antibodies, mixtures of primary and secondary antibodies, at least one of which is fluorescently labeled, mixtures of fluorescently labeled antibodies against multiple antigens, fluorescently labeled lectins, fluorescently labeled proteins A and G, and other fluorescently labeled proteins that bind to cells, tissue structures, and other specific binding agents in a specific manner.

Immunophenotype—the antigenic character of a cell or tissue determined by the functional state of the cell or tissue and the molecules it produces. The presence of particular protein or carbohydrate antigens in a cell is indicative of the genes being expressed by that cell or tissue.

Labeling—whether a specific binding agent is a fluorescent antibody or lectin or other system, a label provides a detectable signal by which binding of the specific binding agent to a structure of interest may be detected. Fluorescence is the term used to describe the light emitted by cells or tissue structures specifically labeled by a fluorophore. Immunofluorescent labeling means utilizing a fluorescent specific binding agent that comprises at least one antibody to specifically label certain cells or tissue structures. Hence immunofluorescence is a particular example of labeling.

Microdissection—a technique for isolating particular cells or other particular tissue portions, such as specific tissue structures, from a tissue sample. Microdissection includes (without limitation) manual microdissection under a microscope using microscopic instruments like the cytopicker described by Beltinger et al. (*Mol. Pathol.*, 51; 233–236, 1998). Microdissection also includes laser assisted microdissection [see for example, Fink et al. (*Lab. Invest.*, 80: 327–333, 2000) and Cerroni et al. (*Br. J. Dermatol.*, 136: 743–746, 1997), both describing the use of a P.A.L.M. UV-laser Robot Microbeam (Mikrolaser Technologie, Bernried, Germany)], combined laser manipulated microdissection and laser pressure catapulting described, for example, by Nagasawa et al., *Kidney Int*, 57: 717–723, 2000 [Laser-manipulated microdissection (LMM) is a method to cut out a single cell or limited tiny region from a specimen under microscopic observation by a laser beam. Laser pressure catapulting (LPC) is a method to push up and collect samples that were microdissected using a strong laser.], and laser capture microdissection using instruments such as the Pixcell System (Arcturus Enginering, Mountain View, Calif.).

RT-PCR—reverse transcription polymerase chain reaction. A technique for converting mRNA to cDNA and then amplifying the cDNA to detect the presence and or quantity of mRNA originally in the sample.

Specific binding agent—an agent that binds substantially only to a defined target. Thus, for example a Tamm-Horsfall protein specific binding agent binds substantially only the Tamm-Horsfall protein. As used herein, the term "Tamm-Horsfall protein specific binding agent" includes anti-Tamm-Horsfall protein antibodies and other agents that bind substantially only to the Tamm-Horsfall protein.

EXAMPLES

The following examples further illustrate the rapid fluorescent labeling methods and microdissection methods. Surprisingly, it has been found that it is possible to a use a sufficient excess of fluorescent specific binding agent to identify target structures (such as cells or organelles) while avoiding an unacceptable loss of biomolecules (such as mRNA) through degradation and/or physical loss. A particular example of the methods is the immunofluorescence-laser capture microdissection (IF-LCM) method. This example uses fluorescent antibodies as the fluorescent specific binding agent and includes protocols for rapid immunofluorescence labeling of desired cells along with optical modifications for immunofluorescence image detection by low light level video microscopy. This rapid staining of cells and tissue structures with immunofluorescent antibodies helps preserve biological molecules, such as DNA, RNA, and proteins. Using this approach, cells and tissue structures can be visualized, identified, and captured to selectively identify and isolate defined portions of tissues that are difficult to identify by light microscopy in unstained tissue. This method permits one to obtain substantially pure populations of specific cells and tissue structures from structurally complex tissues.

Using the rapid IF staining method and the LCM device disclosed herein, excellent delineation of tagged cells, and excellent recovery of mRNA from the tissue sections is achieved. The methods are also particularly useful for retrieving less abundant mRNAs from specific cells and tissue structures. Specific cells may be identified and microdissected by immuno-fluorescence laser capture microdissection. The rapid immunofluorescent reactions can be completed before there is significant loss of mRNA. Low light level detection allows the weakly stained sections to be visualized. This method extends the ability to isolate pure populations of immunotypically defined cells from a sea of similarly appearing cells, and process such cells for further analysis to determine the functional state of the cells.

Particular examples of specific binding agents include antibodies, lectins, protein A, protein G and mixtures thereof. The specific binding agents may carry a detectable label, such as a fluorescent label. The sufficient concentration of specific binding agent may, for example, be at least 0.02 mg/mL, such as at least 0.1 mg/mL. In certain embodiments, the specific binding agent can be prelabeled, for example by mixing a primary antibody and a secondary antibody prior to exposure to the tissue. When at least one of the antibodies is fluorescent, the time of exposure of the tissue to the specific binding agent can be reduced, which in turn can reduce loss of the biomolecule of interest from the tissue specimen.

Certain examples also include using the fluorescent specific binding agents in a sufficient concentration that, when the tissue is exposed to the fluorescent specific binding agent for less than about 5 minutes, the intensified image signal is detectable, so that laser capture microdissection can be performed to substantially isolate target cells that have been labeled. In other embodiments, the fluorescent specific binding agent is present in a sufficient concentration that, when the tissue is exposed to the fluorescent specific binding agent for less than about 3 minutes, the intensified image signal is detectable. In yet other embodiments, the fluorescent specific binding agent is present in a sufficient concentration that, when the tissue is exposed to the fluorescent specific binding agent for not more than about 1 minute, the intensified image signal is detectable.

The microdissection methods of the disclosure can include targeting tissue components with a target laser beam, and viewing the intensified image through an infrared filter that selectively minimizes image distortion caused by the laser beam, without eliminating the signal image. Such filtering is particularly helpful when the image is intensified to such an extent that the laser beam (such as the targeting beam) introduces artifact into the image that may interfere with microdissection. For example, an image intensifier may detect ultraviolet radiation around a target laser beam that creates an apparent enlargement of the targeting beam, and interferes with accurate targeting of cells of interest. However an ultraviolet filter can minimize this distortion.

In more particular examples, tissue specimens are prepared for microdissection by exposing the tissue specimen to at least one fluorescently labeled antibody which specifically binds to a component of interest in the tissue (such as a cell expressing a particular antigen), wherein the tissue is exposed to a sufficient concentration of the antibody or antibodies, in an aqueous solution, for a sufficient period of time to label the component of interest without substantially degrading RNA in the tissue. Unbound antibody is washed from the tissue, and the image of the tissue specimen that has been exposed to the fluorescently labeled antibody or antibodies is intensified, to obtain an intensified fluorescent signal from the tissue. A transfer member is applied to the tissue, and a target laser beam is directed to the component of interest in the tissue, to mark the component that is to be dissected from the tissue specimen, while viewing the target laser beam through an infrared filter that selectively filters infrared radiation but not the fluorescent signal, to minimize distortion of the intensified image, while still viewing the intensified signal. Radiant laser energy is applied to the component of interest, which transfers the component to the transfer member, which may then be removed from the tissue specimen to selectively remove the components that have been irradiated with the laser.

In some embodiments, exposing the tissue to a sufficient concentration of at least one fluorescently labeled antibody comprises exposing the tissue to a concentration of at least 0.04 mg/mL of the fluorescently labeled antibody or antibodies. In other embodiments, exposing the tissue to a sufficient concentration of at least one fluorescently labeled antibody comprises exposing the tissue to a concentration of at least 0.10 mg/mL of the at least one fluorescently labeled antibody or antibodies. In particular embodiments, the tissue is exposed to the antibody or antibodies for less than about 5 minutes, for example less than about 3 minutes, or less than about 1 minute. In other examples, concentrations of antibody can be used that are at least twice as great as recommended for specific labeling of the component of interest. In other examples, concentrations of antibody are used that are 5, 10, 20, 30, 40, 50, 75, or even 100 times as great as normally recommended by a manufacturer for specific labeling.

In particular embodiments of the method for fluorescently staining a tissue section for microdissection, the tissue section is fixed with a non-crosslinking fixative, the tissue section is rinsed twice with an aqueous buffered solution for about 5 seconds per rinse, and the fixed tissue section is incubated with an aqueous fluorescent specific binding agent solution of sufficient concentration to selectively label cells within the tissue section in about 1 minute. The tissue section is then rinsed twice with an aqueous buffered solution for about 5 seconds per rinse, and the tissue section is dehydrated and dried. In more particular embodiments, the aqueous buffered solution is diethylpyrocarbonate-treated phosphate-buffered saline solution. Examples of non-crosslinking fixatives are ethanol, acetone, methanol and mixtures thereof. The fluorescent specific binding agent solution may include an enzyme inhibitor, such as an RNase inhibitor, a DNase inhibitor, a protease inhibitor, and mixtures thereof.

Examples of fluorescent specific binding agents that are used in the specific examples include a primary antibody covalently linked to a fluorescent molecule, a pre-mixed solution of primary antibody and fluorescently labeled secondary antibody, a premixed solution of a fluorescently labeled primary antibody and a fluorescently labeled secondary antibody, a solution of fluorescently labeled lectin, a solution of primary antibody and fluorescently labeled protein A or G, a solution of fluorescently labeled primary antibody and fluorescently labeled protein A or G, and mixtures of such solutions.

Example 1
Low Light Level Detection Systems for Rapid Fluorescence Labeling of Specific Cells and Tissue Structures The microscope in this Example was modified or equipped to stimulate and detect low light level fluorescence from tissue samples labeled with fluorescent specific binding agents.

A typical fluorescence microscope consists of conventional light microscope optics supplemented by an excitation light source (usually a mercury or xenon lamp) and an array of filter cubes. The microscope is typically constructed so that the excitation light passes through the objective along the opposite optical path that fluorescence light takes on its way to the eyepiece or camera. In some embodiments, the microscope is an inverted microscope. In other embodiments, the microscope is a confocal microscope. Fluorescence microscopes may be used to perform manual microdissections, laser-assisted microdissections, and laser capture microdissections.

Manual microdissection of tissue may be performed by using the fluorescence emitted by fluorescent specific binding agents to identify specific cells and tissue structures and then, while viewing the tissue under standard brightfield illumination, cutting the identified cells or tissue structures from the tissue sample using microscopic manual instruments.

In laser assisted microdissection a pulsed laser, such as an ultraviolet (UV) laser, of high beam quality is interfaced with a microscope. An objective focuses the laser beam onto the object plane yielding a beam spot size of less than one micrometer in diameter. The extremely high photon density in the narrow laser focus can be used to sever or ablate biological structures. The principle of laser cutting is a locally restricted ablative photodecomposition process without heating. It is therefore possible to perform microsurgery on cells and molecules, or to microprepare single cells and subcellular particles. Instruments for laser assisted microdissection are, for example, available from Mikrolaser Technologie (Bernried, Germany, www.palm-mikrolaser.com). This type of instrument may be configured for fluorescence microscopy by coupling it to a light source, such as a mercury or xenon lamp, that is directed to the microscope's sample stage. In this manner fluorescence is used to identify cells and tissue structures of interest. It is possible to store the position of the stage exactly and move the laser beam around the selected cells or tissue structure. Afterward, brightfield illumination may be used to direct a micropipette to the location of the selected cells or tissue structure and then the selected portion may be removed by drawing it into the micropipette.

Figure 2A:
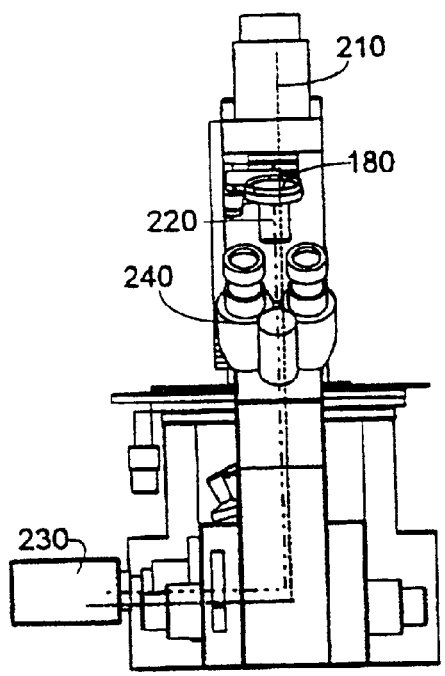
FIG. 2A and FIG. 2B are front and side views of a laser capture microdissection microscope.
Figure 2B:
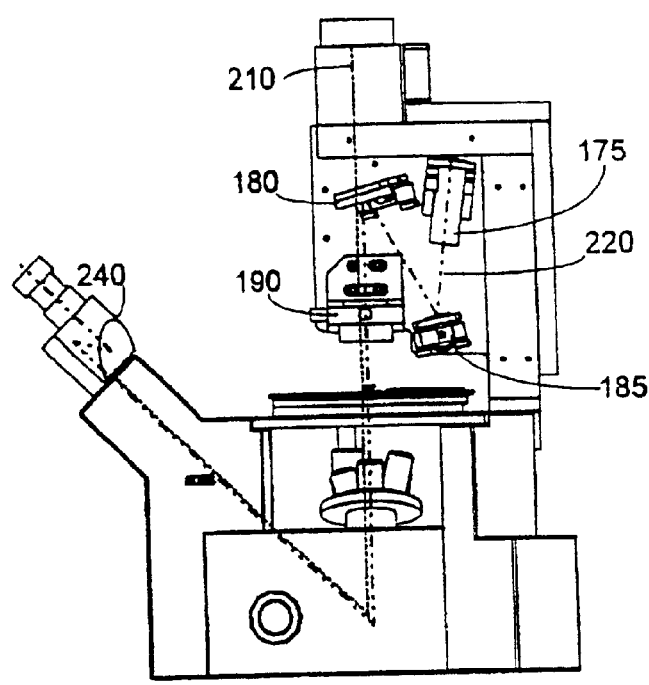

In laser capture microdissection, a capture film is placed over the tissue sample and laser pulses are directed to desired portions of the tissue sample. The laser energy is absorbed by the capture film, which melts and adheres to the underlying portion of the tissue sample. When the capture film is removed, the desired portions of the tissue sample are also removed and may be recovered for study. Examples of instruments for performing laser capture microdissection (LCM) are described in U.S. Pat. No. 5,843,657 to Liotta et al. and in PCT publication WO 98/35216 by Baer et al., both of which are incorporated herein by reference. Instruments of this type are marketed by Arcturus Engineering, Inc. (Mountain View, Calif.) and may be viewed on their Website. FIG. 2 illustrates a typical LCM microscope. Briefly, with reference to FIG. 2, the components of a laser capture microdissection microscope may include a laser light source 175 (such as a combined tracking and capture laser), a dichroic mirror 180, and a beam steering mirror 185 to direct the capture laser light through a focussing lens 190 toward the sample stage. The LCM instrument typically includes a white light illumination path 210 and a laser beam path 220. Both of the paths typically include delivery of optical information to an image acquisition system 230 or to a binocular or monocular set 240.

The rapid fluorescent specific binding agent labeling methods of the present disclosure produce images that are dimmer than images produced by samples treated with fluorescent specific binding agents according to conventional methods. Therefore, an image intensifier or a charge coupled device (CCD) capable of low light level detection, such as an intensified charge coupled device (ICCD), is helpful to view these images. In some embodiments, an image intensifier is placed between the sample stage and a video camera or eyepiece of either a standard fluorescence microscope used for manual microdissection, a laser assisted microdissection microscope, or an LCM microscope. In more particular embodiments the image acquisition system 230 of the LCM microscope of FIG. 2 is replaced with a low light level detection system as illustrated in FIG. 3.

Figure 3:
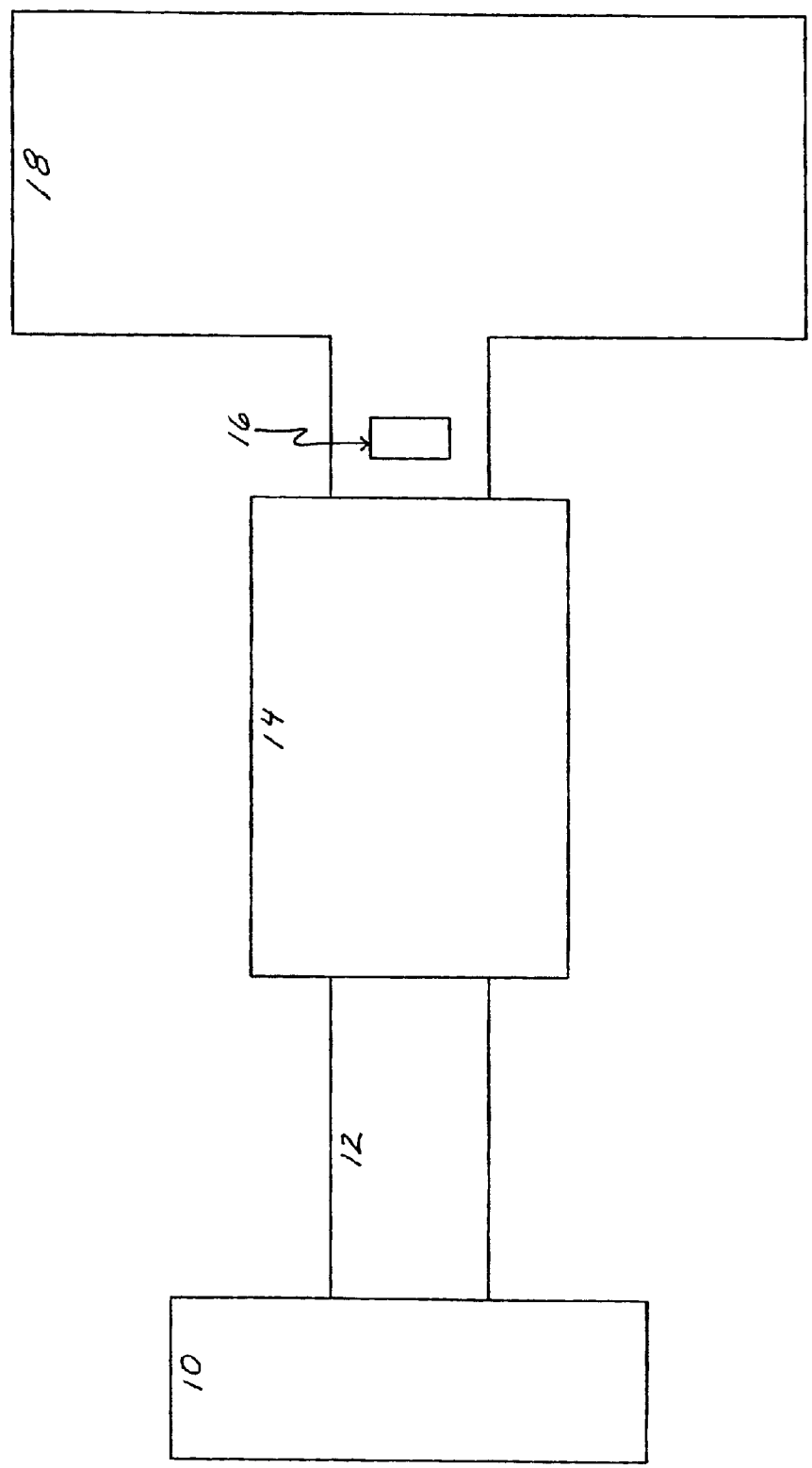
FIG. 3 is a schematic diagram showing an example of a low light level detection system.

With reference to FIG. 3, the low light level detection system may include an image acquisition system 10 (such as a video camera or CCD), a relay lens 12 (which serves to focus the image emerging from the image intensifier onto the image plane of the image acquisition system) and an image intensifier 14. In some embodiments an optional heat (IR radiation) absorbing filter 16 may be positioned to prevent light from the tracking and capture lasers from reaching the image intensifier 14. The low light level detection system is optically connected to the microscope 18 so that the image from the microscope is focussed onto the image plane of the image intensifier 14.

In certain embodiments, image intensifiers function to increase the number of photons available in the output in response to the arrival of photons at the input. Image intensifiers are also known as imaging tubes or image-converting tubes and include those of the types disclosed in U.S. Pat. No. 4,628,273 to Vlasak, U.S. Pat. No. 5,146,296 to Huth, U.S. Pat. No. 5,369,267 to Johnson et al. U.S. Pat.

No. 5,349,177 to Thomas et al., U.S. Pat. No. 5,510,673 to Wodecki et al., U.S. Pat. No. 5,742,115 to Gertsenshteyn, U.S. Pat. No. 5,994,824 to Thomas et al., and U.S. Pat. No. 6,040,657 to Vrescak et al. Image intensifiers are available from Photek Inc. (Tucson, Ariz.), DEP (Roden, The Netherlands), and Optical Elements Corporation (OPELCO, Dulles, Va.). Generation IV intensifiers are the best image intensifiers currently available and are based on gallium arsenide photocathode technology and small-diameter microchannel plates. When a generation IV intensifier is coupled to a high-performance ICCD (intensified charge coupled device) system, single-molecule fluorescence may be detected. Such a system, the I-PentaMAX, is available from Roper Scientific (Trenton, N.J.). However, any type of image intensification can be used.

To demonstrate some of the rapid fluorescent binding agent labeling methods and microdissection methods, a Pixel II LCM microscope (Arcturus Engineering Inc; Mountain View, Calif.) was modified for fluorescence excitation, low light level image detection, and transmitted light image detection. The fluorescent excitation light was provided by a mercury light source (BH2-RFL-T3, Olympus, Tokyo, Japan) and a FITC filter cube (OM-XF 100, Opelco, Sterling, Va.). The low light level fluorescence image was captured by an image intensifier (KS-1380; Opelco, Sterling, Va.) coupled to a video camera (CCD 72, Dage MTI, Michigan City, Ind., or Model 1322-1000, Coho, San Diego, Calif.) on the side port of the microscope. The KS-1380 image intensifier consists of a high gain, microchannel plate image enhancer coupled by a relay lens assembly to an image acquisition system. In this case the image was acquired by the video camera (FIG. 3). The KS-1380 intensifier adds $10^4$ to $10^5$ gain (i.e., it multiplies the number of photons reaching the intensifier about 10,000 to over 100,000 times and transmits them to the image acquisition system) to the detection system and enables visualization of low light levels emitted by the cells labeled, according to the methods of the present disclosure, with fluorescent specific binding agents. Standard transmitted light color images were recorded with a color video camera attached to a triocular microscope head (Olympus, Melville, N.Y.).

The KS-1380 image intensifier was very sensitive to the light from the tracking laser used to focus the capture laser onto specific cells and intense blooming (enlarging) of the laser image on the intensifier. Blooming interfered with accurate microdissection because it made it difficult to tell exactly where the capture laser would hit the sample. To solve this problem, a pair of infrared heat blocking filters (51962, Oriel, Stratford, Conn.) were placed between the intensifier and the microscope to decrease the intensity of the tracking laser and prevent blooming of the laser spot. However, it is not essential that two filters are used. A single filter having a higher infrared absorbance or more than 2 filters each with a lower infrared absorbance may be used. The filters, as placed, served to protect the image intensifier from laser light induced damage, and advantageously allowed focussing of the tracking laser using the same imaging system used to identify the fluorescently tagged cells.

Alternatively, an image intensifier that is not sensitive to the laser light, for example less sensitive to red wavelengths, could make it unnecessary to include an infrared absorbing filter or filters. Another alternative to using the infrared absorbing filter or filters is to use a filter, such as an interference filter, specifically designed to eliminate light at the laser wavelength, such as 812 nm, corresponding to the wavelength emitted by a He—Ne laser. The image intensifier was for demonstration purposes typically operated at about ⅓ of maximum gain, but could for example be operated at any fraction of maximum gain, such as one eighth, ¼, ½, ¾, or at maximum gain depending upon the intensity of fluorescence being emitted by the fluorescent specific binding agent used to label the tissue section.

The low light-level video system used to demonstrate the method easily detected the fluorescent light generated by both conventional and rapidly stained immunofluorescent samples. Although fainter signals could potentially be detected, detection of immunofluorescently labeled cells appeared to be limited more by non-specific labeling of surrounding tissue than by the weakness of the specific signal. Images with marginal signal to background signals can be amplified by adjusting the dark current of the video camera so that the background non-specific binding becomes black.

Image processing is another type of signal intensification. Images from the video camera may, for example, be captured and averaged by image processing to further enhance the contrast between the background and the specifically labeled cells. Other image enhancement techniques, including false color schemes that enable the visualization of slight differences in fluorescence intensity, can also increase the imaging system's sensitivity and enable the use of shorter binding times and weaker specific binding agents, such as weak antibodies. Image enhancement and frame capture and averaging software packages useful for image enhancement include Optimas 6.5 (Media Cybernetics, Silver Spring, Md.) MetaFluor (Universal Imaging Corp., West Chester, Pa.) and Image (National Institutes of Health, Bethesda, Md.). A computer based system, capable of performing manipulation and enhancement of microscopic images in real time, is described in Walter and Berns, *Proc. Nat. Acad. Sci.*, 78: 6927–6931, 1981.

Example 2

Qualitative Changes in RNA Levels on Exposure to Aqueous Conditions

Figure 4:
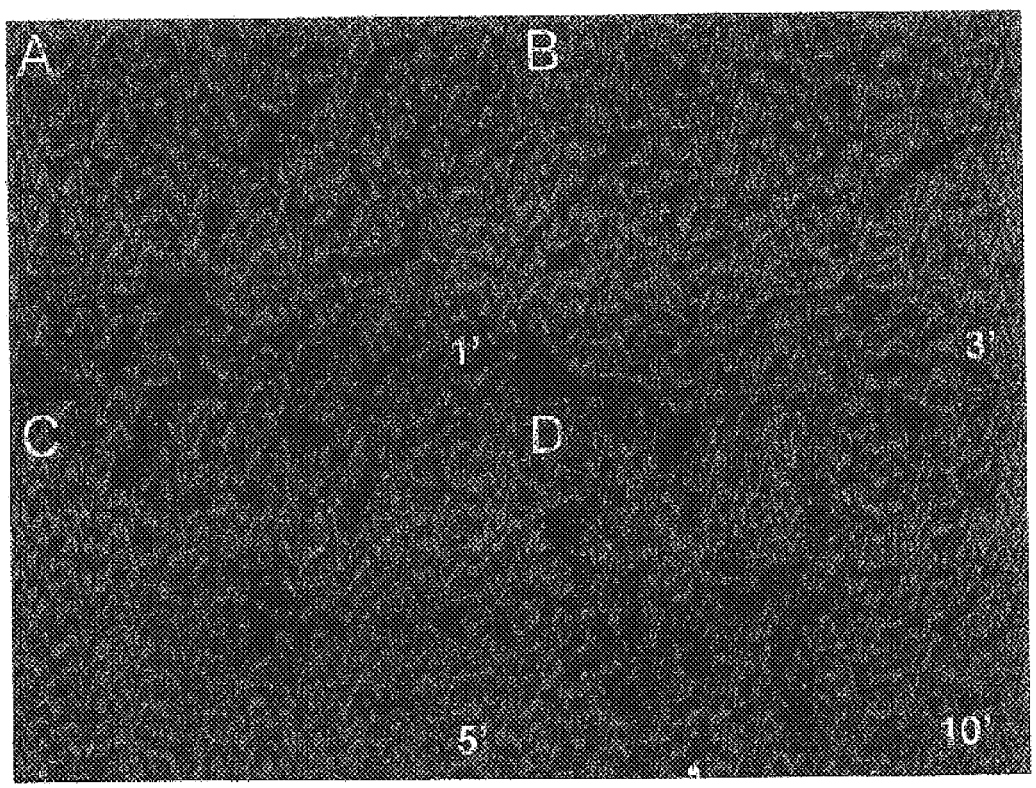
FIGS. 4A, 4B, 4C and 4D are a series of photomicrographs that show the time course of RNA disappearance in aqueous solution as followed by staining with acridine orange. In this black and white image, the loss of mRNA that occurs as the length of water incubation increases, corresponds to an increase in the number of white spots (compare, for example, panels A and C).

The reduction of RNA and mRNA levels that occurs when tissue is exposed to aqueous conditions in vitro was followed by measuring total tissue RNA using acridine orange which stains RNA orange. Reduction of levels can occur by degradation of RNA and mRNA by nucleases in the aqueous solution, or even by physical loss of the RNA (or other biomolecule) from the specimen during the labeling process (which includes labeling and washing). FIG. 4 shows that tissue RNA decreases rapidly under these conditions.

Sections of mouse kidney were fixed in ice cold acetone, incubated in DEPC (diethylpyrocarbonate)-treated water for 1 minute (panel A), 3 minutes (panel B), 5 minutes (panel C), and 10 minutes (panel D) at room temperature, then rapidly stained with 0.02% acridine orange (2 mg in 10 mL 0.067M phosphate buffer, pH 6.0). After washing with PBS/DEPC-treated water (pH 6.0) for 30 seconds the sections were examined using a UV filter cube and the images captured with a color video camera.

Figure 5:
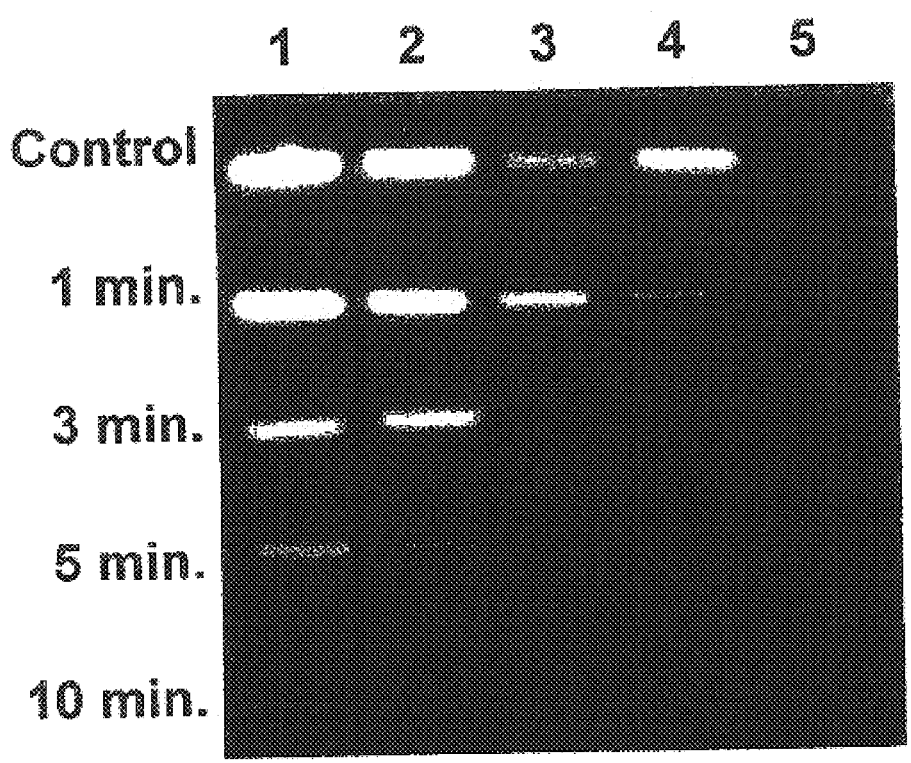
FIG. 5 shows the time course of RNA disappearance as followed by RT-PCR (reverse transcription polymerase chain reaction). Successive columns represent serial 1:10 dilutions.

The disappearance of mRNA in aqueous solution was also followed using semi-quantitative RT-PCR for malate dehydrogenase (MDH) mRNA. The results are shown in FIG. 5. Cryosections (2 $\mu$m) of a mouse kidney were exposed to DEPC-treated water for 0 (control), 1, 3, 5, or 10 minutes, dehydrated and air dried, then manually scraped with a clean razor blade. The RNA was extracted, and RT-PCR performed for MDH mRNA. Columns in FIG. 5 are successive 1:10 dilutions of cDNA obtained from the entire section. MDH mRNA was not detected in the 1 minute sample processed without RT (data not shown).

The semi-quantitative RT-PCR results demonstrate that 1 minute exposure to aqueous solutions (without RNAse) had the best preservation of tissue mRNA. The different time courses of tissue total RNA (by acridine orange) and tissue mRNA (by RT-PCR) suggest that perhaps RNAse-induced degradation of mRNA is faster than physical loss of RNA from the tissue. However, rapid immunofluorescent staining (or other labeling) as disclosed herein reduces the disappearance of the RNA.

In addition, acridine orange staining is useful as a screening method for detecting relative RNA preservation. For example, sections or blocks lacking orange color would not be used for microdissection. However, some loss can occur in sections with orange color because tissue mRNA is lost more rapidly than tissue RNA. Hence acridine orange staining can be used as a rapid and convenient assay to determine a time period during which rapid labeling can be performed while preserving a desired amount of RNA to perform microdissection.

Example 3
Rapid Labeling Methods Utilizing Fluorescent Specific Binding Agents

Preservation of mRNA and other biological molecules during tissue fixation, sectioning, and histochemical staining has been achievable because these steps can be performed in non-aqueous solutions. However, it has not been known how to identify cells by labeling with solutions of fluorescent specific binding agents while simultaneously preserving biological molecules such as RNA, DNA, lipids, secondary metabolites, and proteins, particularly RNA, DNA, and proteins, and in particular mRNA. For example, the present specification shows that exposure to aqueous labeling solutions for more than about five minutes is sufficient to result in an almost total loss of tissue RNA, especially mRNA (Example 2; FIGS. 4 and 5).

In some embodiments, rapid methods for labeling cells and tissue structures with fluorescent specific binding agents are combined with low light level detection of fluorescence emitted by the fluorescent specific binding agents. The combination makes it easier to reduce the time a tissue sample is exposed to aqueous conditions to less than about 5 minutes, or less than about 3 minutes, or not more than about 1 minute and thereby substantially preserve biological molecules within the tissue sample (see Example 5). Intensification of the image permits lower exposure times to provide fainter label signals, which can still be detected in the intensified image.

Fixation of the tissue sample prior to labeling with fluorescent specific binding agents may be accomplished with either cross-linking or non-cross-linking fixatives. Cross-linking fixatives function by making chemical bonds between proteins in the tissue sample, leading to their precipitation and immobilization within the tissue. Cross-linking fixatives include formaldehyde and paraformaldehyde. Non-cross-linking fixatives do not chemically alter the proteins in the sample; rather they simply precipitate them where they are found in the tissue sample. Non-cross-linking fixatives include ethanol, acetone, methanol and mixtures thereof. In some embodiments, acceptable tissue morphology and optimal mRNA recovery is obtained with frozen tissue that is fixed with a non-cross linking fixative and lightly stained with H&E (see, Kohda et al., *Kidney Int.*, 57: 321–331, 2000 and Goldsworthy et al., *Mol. Carcinog.*, 25: 86–91, 1999). In other embodiments, tissue embedded in paraffin is utilized. Cross-linking fixatives, such as formaldehyde, may also be utilized with the present methods, but subsequent protein identification will be more difficult, especially if it is based upon a molecular weight determination. In addition, formaldehyde may also decrease the likelihood that antibody will bind antigen.

High concentrations of fluorescent specific binding agent are used in some embodiments to reduce the aqueous exposure time of a tissue sample and yet, surprisingly, allow sufficient fluorescent labeling to enable low light level identification of specific cells within a tissue sample and effective microdissection of the sample. Alternatively, non-aqueous labeling solvents can be used. Reduction of labeling time is believed to be useful with both aqueous and relatively non-aqueous labeling solutions (such the solution of antibody that is used for immunofluorescent labeling). Predominantly aqueous solutions are those that contain more than 50% water, while a substantially non-aqueous solution is one which is substantially free of water (for example, is not more than 30%, 20%, 10%, 5%, 2%, or even 1% water).

A concentration of fluorescent specific binding agent that is sufficient to reduce the labeling time (such as aqueous exposure time) of a tissue sample to substantially prevent loss of biological molecules from the sample, yet enable low light level identification of specifically labeled cells and tissue structures within the tissue sample to enable microdissection, may be arrived at by first determining the loss of the biological molecule of interest as a function of the time the tissue sample is exposed to a solution similar to that used to deliver the fluorescent specific binding agent. For example, it is possible to expose several representative tissue samples, for various periods of time, to a solution that is similar to the medium in which the fluorescent specific binding agent will be applied to the sample. For instance the tissue sample may be exposed to such a solution for 30 seconds, 1 minute, 3 minutes, 5 minutes and 10 minutes, and then quickly dehydrated. The dehydrated samples may then be assayed for the amount of the biological molecule of interest remaining after each of the time periods. If the biological molecule of interest is lost from the sample quickly, for example in less than about 1 minute, a higher concentration of fluorescent specific binding agent and a short exposure time, such as 30 seconds may be utilized for labeling. If on the other hand the biological molecule of interest is lost somewhat more slowly, for instance after exposure to the solution for more than about 3 minutes, the concentration of fluorescent specific binding agent used for labeling may be somewhat lower and the exposure time longer, such as 2 minutes. In either case, the amount of loss that can be accepted will also factor into the concentration of fluorescent specific binding agent and the time of exposure that is used. If, for example, 50%, 60% or 70% loss is tolerated, the concentration of fluorescent specific binding agent can be lower and the exposure time greater than if only 10%, 5% or 1% loss is acceptable.

Having determined the rate of loss of the biological molecule of interest and the desired exposure time, the concentration of fluorescent specific binding agent that enables a short enough time of exposure to preserve the biological molecule of interest, and yet specifically labels the cells or tissue structures of interest, may be determined empirically. A useful starting point for the determination is the recommended dilution ratio at which the fluorescent specific binding agent is used for conventional fluorescence labeling. A concentration that is 10 to 100 fold (including 20, 30, 40, 50, 60, 70, 80 and 90 fold), for example 10 to 80 fold, such as 10 to 60 fold or 10 to 30 fold greater than the recommended dilution may be used to label the sample within the desired period of time. For example, if the recommended dilution is 1:400, the starting dilution would be in the range of about 1:40 to about 1:4 (10 to 100 fold greater than recommended), for example from 1:40 to 1:5, such as from 1:40 to 1:7 or 1:40 to 1:13. The labeled sample may then be viewed with a low light level detection system to determine if it is possible to identify specifically labeled cells or tissue structures within the sample. If it is not possible to identify specifically labeled cells or tissue structures, a second sample labeled for the same amount of time, but with a greater concentration of fluorescent specific binding agent, for example two-fold to ten-fold, such as three-fold greater than was initially used, is viewed to see if it is now possible to identify specifically labeled cells. This is repeated until satisfactory labeling is accomplished in the amount of time that preserves the desired amount of the biological molecule. Such empirical determinations of appropriate concentrations of specifically labeling cell and tissue samples with specific binding agents are disclosed, for example, in Harlow and Lane, *Using Antibodies*, pp. 137, Cold Spring Harbor Press, 1999.

Fluorescent specific binding agents, such as commercial antibody or lectin preparations that are not affinity purified, are typically available in solutions having a concentration from about 1 mg/mL to about 100 mg/mL in total protein and will contain varying amounts of the desired binding agent. These solutions are typically diluted for immunofluorescence by about 1:50 to about 1:2000, such as between 1:100 and 1:1000, depending upon the actual titer of antibody. These numbers imply that the total protein concentration used for conventional fluorescence can vary from about 0.5 µg/mL to about 2000 µg/mL, for example from about 5 µg/mL to about 1000 µg/mL, such as from about 50 µg/mL to about 500 µg/mL. Accordingly, assuming for example the use of a 10-fold higher concentration, the total protein concentration for the rapid methods will be in the range from about 5 µg/mL to about 20 mg/mL, for example from about 50 µg/mL to about 10 mg/mL, such as from about 0.5 mg/mL to about 5 mg/mL.

A useful way to determine the dilution factor that provides a sufficient concentration of fluorescent specific binding agent to reduce the exposure time to a time that substantially preserves a biological molecule is to first determine the dilution factor that yields good results with a conventional fluorescent specific binding agent protocol. If the specific antibody concentration of the antibody is unknown, prepare and test 1/10, 1/100, 1/1000, and 1/10,000 dilutions of the stock solution (Harlow and Lane, *Using Antibodies*, pp. 138, Cold Spring Harbor Press, 1999). Once the appropriate dilution for conventional fluorescence specific binding agent labeling is known, the dilutions for the rapid methods of the present disclosure are calculated to provide from about 10 to 100 fold greater concentrations. This is a starting point and the concentrations may be adjusted upward if specific cells or tissue structures are insufficiently labeled within the time period determined by the rate of loss of the desired biological molecule.

Monoclonal antibodies are often applied as tissue-culture supernatants. Such supernatants are used undiluted and have specific antibody concentrations from about 20 µg/mL to about 50 µg/mL. Given that useful antibody concentrations for the rapid labeling methods are typically at least 10 to 100 fold more concentrated, specific antibody concentrations will be at least 200 µg/mL, for example 1 mg/mL, such as 2 mg/mL.

Another aspect of the rapid fluorescence labeling methods is the use, in certain embodiments, of pre-mixed primary and secondary antibodies (one or both of which are fluorescent) to shorten the time the tissue sample is exposed to aqueous solutions of the fluorescent specific binding agent. By combining the secondary antibodies with the primary antibodies and allowing the secondary antibodies to bind to the primary antibodies before labeling, the need for a separate incubation with the secondary antibody is eliminated. In other embodiments fluorescent protein A or protein G are pre-mixed with a primary antibody (fluorescent or not) to which they bind specifically.

Aqueous washes of a tissue sample may be shortened to further reduce aqueous exposure of tissue samples and thereby preserve larger amounts of biological molecules. A lower limit on how short the aqueous washes may be is determined, for example, by observing the amount of background fluorescence emitted using a low light level detection system. If the cells or tissue structures are insufficiently washed it may be difficult, even with image enhancement, to discern specifically labeled cells and tissue structures from the background fluorescence emitted by non-specifically labeled cells and tissue structures. If this occurs, the wash time may be increased. The combined time of exposure of a tissue sample to aqueous fluorescent specific binding agents and to aqueous wash solutions place an upper limit on the length of the washes.

Example 2 illustrates how a combined aqueous exposure time that does not exceed about 5 minutes, for example about 3 minutes, such as no more than about 1 minute, may be used to preserve biological molecules, for example, mRNA. In some embodiments, washing comprises rapidly dipping a slide bearing the tissue sample in and out of a wash solution within 5 seconds. Useful solutions for washing the tissue sample include, but are not limited to, phosphate-buffered saline (PBS), distilled water, diethylpyrocarbonate (DEPC) treated water, Tris-buffered saline (TBS), ethanol-water solutions, RNAsecure™ (Ambion, Austin, Tex.) and mixtures thereof. The wash solution may also include a surfactant, such as a nonionic detergent, for example Tween 20, 40, 60, 80, or 100.

It is also possible to reduce loss of biological molecules by using solutions of fluorescent specific binding agents prepared with non-aqueous solvents, or solvents with reduced concentrations of water. For instance, such solvents capable of dissolving a sufficient amount of the fluorescent specific binding to specifically label cells or tissue structures may be utilized. Examples of such solvents include methanol, ethanol, isopropanol, and acetone, which can be substituted partially or completely for water in a labeling (e.g. antibody) solution. In kind with the method of determining the time course of loss of biological molecules from the tissue sample using an aqueous solution, the time course of loss of biological molecules in non-aqueous solution may be determined, and a sufficient concentration of fluorescent specific binding agent may be determined empirically, also in kind with the methods above.

Advantageously a mixture of non-aqueous solvents and water may be utilized to deliver the fluorescent specific binding agent to the tissue sample. For example mixtures of non-aqueous solvent and water containing more than about 20% water, for example more than about 50% water, such as more than about 75% water may be used. A particular example is 25% ethanol in water. Again, the time course of loss of biological molecules in this system may be determined by assaying for the biological molecule of interest at various times. Because non-aqueous solvents tend to reduce the ability of specific binding agents to bind to their targets, each fluorescent specific binding agent may be tested for its effectiveness in the solvent system. Regardless, for those fluorescent specific binding agents that are still able to bind specifically in such solvent systems, the reduction in water content may help to farther reduce loss of biological molecules from a tissue sample.

The rapid labeling and washing protocols of the present disclosure enable completion of the aqueous phase steps in as little as about 5 minutes, for example about 3 min, such as 1 minute. Surprisingly, the protocols still yield excellent immunofluorescent labeling (Example 4, FIG. 6) and, despite the high concentrations of fluorescent specific binding agents utilized, excellent mRNA recovery (Example 5, FIG. 8).

In certain embodiments it may also be desirable to include degradative enzyme inhibitors, such as RNase inhibitors, DNase inhibitors, protease inhibitors and mixtures thereof in the aqueous solutions to reduce loss of biological molecules by enzymatic degradation.

Example 4
IF-LCM: Laser Capture Microdissection of Immunofluorescently Defined Cells Functional genomics and proteomics can now be brought down to the level of individual cells in a tissue. Analysis of protein and mRNA levels within specific cells and tissue structures will help determine whether and to what extent genes are operative in normal versus diseased cells. Isolation of specific cells will make it possible to detect somatic mutations in cellular DNA that result in malignancy. Researchers will be able to follow changes in gene expression that accompany cell maturation, tumorigenesis, and cell apoptosis. Such studies will also make it possible to design therapies based upon suppression of certain gene products. Furthermore, specific protein products produced by diseased cells may be identified and used to develop new diagnostic methods that scan for the presence of such proteins. All of these things will be advanced by an effective method for selectively identifying and isolating cells from tissue samples without losing biological molecules, such as DNA, RNA, and proteins, and in particular mRNA. With a unified picture of the DNA structure, overall and specific RNA levels, and protein levels in particular cells, the molecular nature of many disease states can be better understood.

The some embodiments, the disclosure provides a rapid cell and tissue structure specific fluorescence laser capture microdissection method that is effective for identifying and isolating pure cells and tissue structures from even complex tissue sections. The disclosure enables targeted analysis of gene expression in specific cells because it successfully preserves biological molecules such as DNA, RNA, and proteins, and in particular mRNA.

To demonstrate the method, selective fluorescent LCM was used to isolate thick ascending limbs (TALs) from kidney tissue. The kidney is an anatomically complex organ with exceptional cellular heterogeneity and thus serves as an excellent model to demonstrate the power of the IF-LCM technique for identification and isolation of cells from complex tissues.

Kidney tissue was obtained from 6 week-old female Balb/c mice that were purchased from the National Institutes of Health, Bethesda, Md. All animals had free access to water and food and all animal procedures were approved by the National Institute of Diabetes and Digestive and Kidney Diseases Animal Care and Use Committee. The mice were anesthetized with 100 mg/kg ketamine, 20 mg/kg xylazine, and 10 mg/kg acepromazine injected i.m. Both kidneys were harvested from each mouse and immediately frozen with OCT Compound (62550, Sakura-Finetek, Calif.).

Freshly frozen tissue sections were fixed for 2 minutes with cold acetone then washed twice, 5 seconds each, with diethyl pyrocarbonate (DEPC)-treated phosphate buffered saline (PBS) pH 7.6.

The sections were incubated with premixed primary and secondary antibody for 1 minute. In this instance, the primary antibody was monoclonal anti-Tamm-Horsfall protein antibody (CL1032A, Accurate Chemical & Scientific Corp., Westbury, N.Y.); the secondary antibody was fluorescent goat anti-mouse IgG antibody (A-11029, Molecular Probes, Eugene, Oreg.). High concentrations of primary antibody (1:20 dilution; 20-fold greater than routine immunohistochemistry), secondary antibody (1:7 dilution), and RNAse inhibitor (400 units/mL; N251A, Promega, Madison, Wis.) were premixed for 10 minutes at room temperature. Following labeling, the sections were washed rapidly two times for 5 seconds each with PBS/DEPC at room temperature, dehydrated, and air dried. Slides were viewed with a FITC filter cube and low light level video microscopy as described in Example 1. ALEXA-conjugated secondary antibodies were used because the fluorescent signal survives the ethanol and xylene dehydration steps. Specific portions of the histologic section were affixed to transfer film (CapSure TF-100; Arcturus Engineering Inc) by brief laser pulses. As controls, sections were incubated with a different primary antibody (M085, DAKO, Campinteria, Calif.), or with only the secondary antibody.

Figure 6:
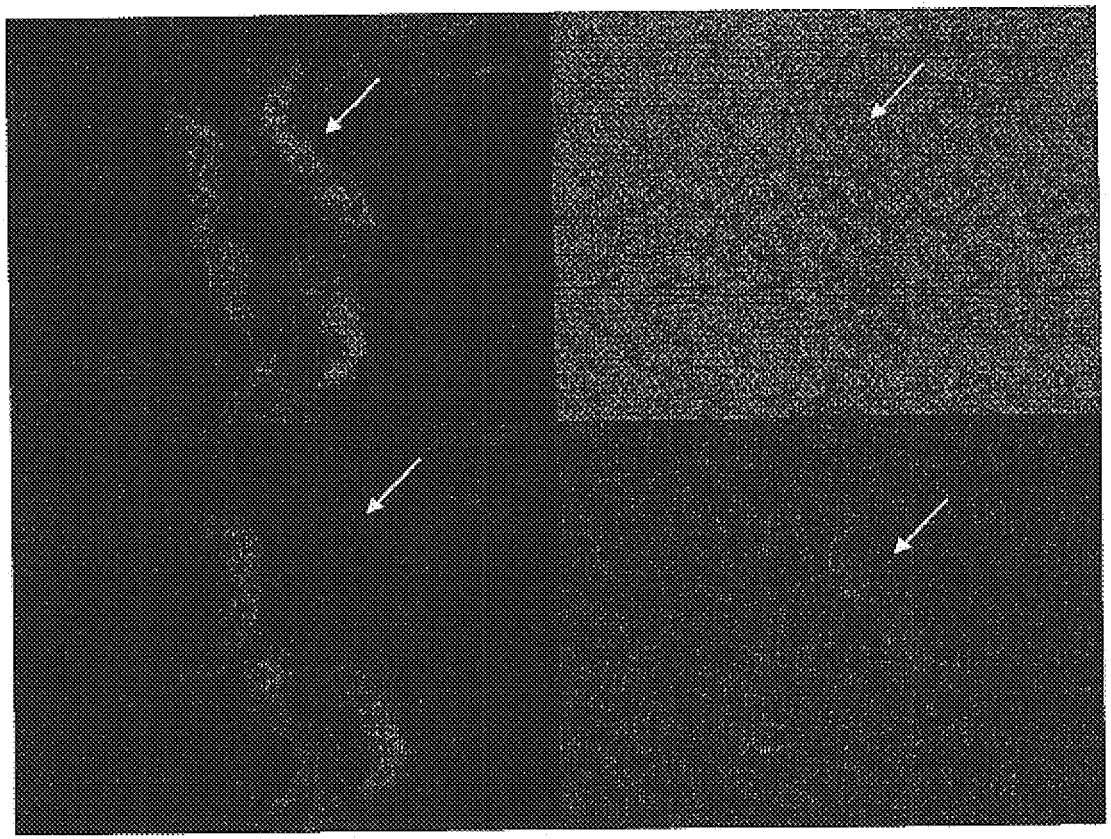
FIGS. 6A, 6B, 6C and 6D are a series of photomicrographs that illustrate LCM capture of immunofluorescently stained mouse kidney. Panels A and B show the immunofluorescent and transmitted light image before transfer, respectively. Panel C shows the fluorescent image of the tissue section after dissection. Panel D shows a fluorescent image of the thick ascending limb (TAL) recovered on the transfer film. The arrow indicates the transferred area.

FIG. 6 shows the detection, transfer, and recovery of outer medullary thick ascending limbs by IF-LCM. Anti-Tamm Horsfall Protein (THP) was chosen because it specifically stains thick ascending limbs. The thick ascending limbs were difficult if not impossible to detect in unlabeled frozen sections examined by transmitted light (FIG. 6, panel B), but easily seen by immunofluorescence after labeling with THP (FIG. 6, panel A). The labeled portion of the tubule was transferred by overlapping 7.5 $\mu$m laser spots (FIG. 6, panels C and D). There was no apparent contamination by surrounding tissue at the level of light microscopy (FIG. 6, panel D). In control experiments (data not shown), labeling of the TAL was not detected with either omission of the primary antibody, or with a different secondary antibody (monoclonal anti human-smooth muscle actin antibody). The latter antibody did stain smooth muscle cells in the media of renal blood vessels.

Figure 7:
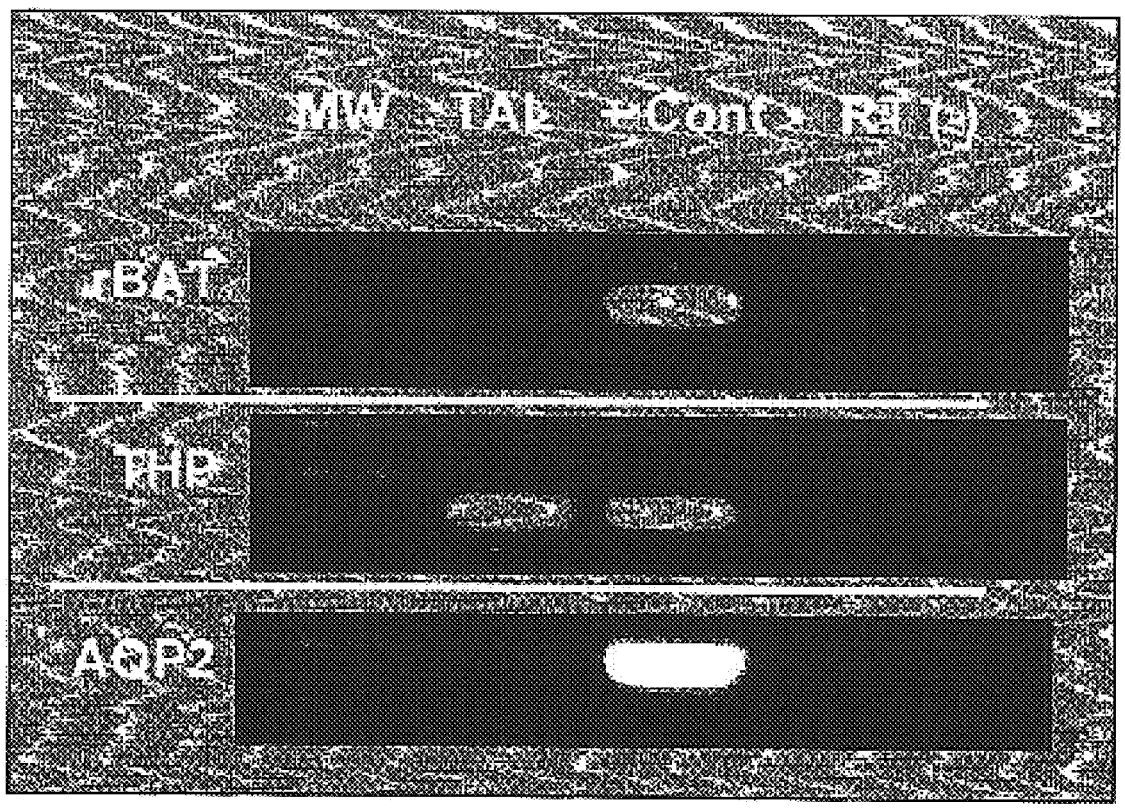
FIG. 7 illustrates the specificity of immunofluorescent staining combined with LCM capture by presenting the Southern blot RT-PCR analysis of 3 genes in a TAL sample isolated by LCM. Microdissected mouse outer medullary TALs were obtained as in FIG. 6. See table 1 for details of PCR primers and reaction conditions. Abbreviations: rBAT (basic amino acid transporter), THP (Tamm-Horsfall Protein), and AQP-2 (aquaporin-2). The positive control (+cont) consisted of a pooled sample of RNA harvested from a scraped section from the same block. Negative control [RT(−)] represents the total RNA from microdissected TAL analyzed without reverse transcriptase.

To further demonstrate that the combination of rapid fluorescent specific binding agent labeling, low light level visualization, and LCM can be used to selectively isolate thick ascending limbs from kidney tissue, microdissected sections of a kidney tissue sample were tested using RT-PCR with a panel of 3 genes. The 3 specific genes that were assayed are expressed in a segment specific fashion within kidney tissue: basic amino transporter (BAT) expressed in proximal convoluted and straight tubules, Tamm-Horsfall protein (THP) expressed only in TAL, and aquaporin-2 (AQP-2) expressed only in the collecting duct system. THP was detected as expected (FIG. 7), but BAT or AQP-2 were not detected, indicating that the microdissected cells were not contaminated by surrounding proximal tubules (BAT) or collecting ducts (AQP-2). This demonstrates that the cells were thick ascending limb cells, thus confirming the specificity of the cell identification and microdissection.

Example 5
Recovery of mRNA from Microdissected Tissue

The recovery of mRNA following conventional hematoxylin & eosin (H&E) staining LCM was compared to the mRNA recovery after rapid labeling with fluorescent specific binding agent according to the methods described herein. Alternative sections of the same tissue block were stained with rapid H&E, the rapid fluorescent specific binding agent labeling protocol, or fixed with acetone and dehydrated (without exposure to aqueous solutions, Control), scraped, and RT-PCR performed for MDH mRNA.

The rapid fluorescent labeling was performed as described in Example 4. Hematoxylin-Eosin staining was accomplished by fixing the tissue section with 70% ethanol for 2 minutes, washing with DEPC-treated water for five seconds, staining with Hematoxylin stain (CS 401-1D, Fisher Scientific) for 30 seconds, washing with DEPC-treated water for 10 seconds, dehydrating with an ethanol gradient, and counter-staining with alcoholic Eosin Y solution (HT 110-1-16; Sigma Chemical Co., St. Louis, Mo.) for 30 seconds. Sections were then washed three times with 100% ethanol, two times with xylenes, and air dried.

Total RNA was extracted from H&E and rapid fluorescent labeled samples using GTC/phenol-chloroform. The samples were incubated with 200 µL of 4 M guanidine thiocyanate, 25 mM Na$_3$citrate, 0.5% sarcosyl, and 0.72%-mercaptoethanol for 10 minutes at room temperature. After centrifuging the samples, the GTC solution was removed to a new 500 µL test tube and 200 µL of the phenol-chloroform was added. Samples were vortexed and centrifuged 30 minutes at 4° C. The aqueous layer was transferred to a new 500 µL test tube and extracted again with phenol-chloroform. The samples were washed with chloroform and precipitated with isopropanol. Samples were frozen for 1 hour at −80° C. and centrifuged 40 minutes. Samples were then washed successively with 70% ethanol and 100% ethanol, then air-dried. Sample RNA was resuspended with 10.5 µL of resuspension solution (7.1 mM DTT, 1.7 units/µL recombinant RNase inhibitor in DEPC treated water).

Seven µL of the RNA solution was denatured at 60° C. for 10 minutes and mixed with 12 µL of RT master mix (final concentration 3 mM Mg2+, 1 mM dNTP, 5 mM DTT, 1.35 U/µL RNasin, 5 µM oligo dT15) with 1 µL (200 units) of MMLV-RT (Promega). RT reaction was performed at 42° C. for 60 minutes. The remainder of the RNA solution was processed without reverse transcriptase (-RT). RT products were used as a template for PCR. Primer sets (see Table 1) that hybridized to different exons were chosen and produced a single correctly sized band. Since the BAT primer set was in the same exon, a portion of the RNA sample was treated with DNAse I for 1 hour. PCR reactions contained 1 mM primers, 1–1.5 mM Mg2+, 200 µM deoxynucleotide triphosphates, reaction buffer, and 1.5 units Taq DNA polymerase (Promega) in a final volume of 25 µL. PCR was performed using 35 cycles of 94° C. for 45 seconds, 55° C. for 45 seconds, and 72° C. for 75 seconds. Reaction products were size fractionated by gel electrophoresis and stained with ethidium bromide (FIG. 8).

Figure 8:
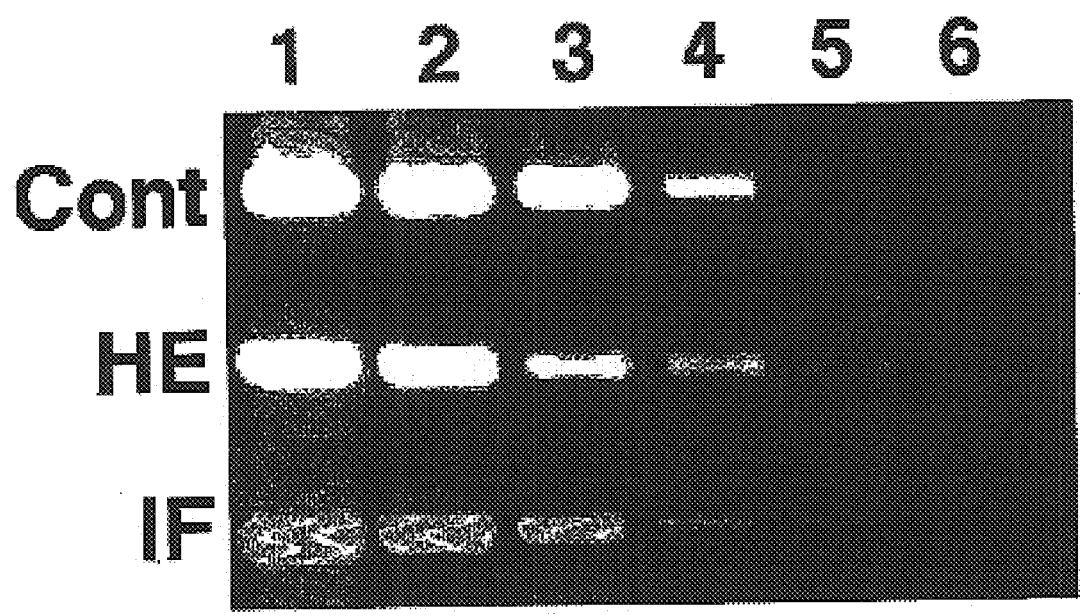
FIG. 8 compares the recovery of malate dehydrogenase (MDH) mRNA following the rapid fluorescent specific binding agent labeling method of this disclosure with hematoxylin and eosin (H&E) staining and a control that was never exposed to aqueous solutions. Successive columns represent serial 1:10 dilutions.

The semi-quantitative RT-PCR confirmed that the two procedures had similarly excellent preservation of tissue RNA levels (FIG. 8). Rapid H&E staining is recognized as a method of staining that substantially preserves biological molecules. This may be seen by comparing the RT-PCR results for the control to those for the H&E stained sample. By comparison, based upon the gel shown in FIG. 8, the rapid method of labeling cells and tissue structures with fluorescent specific binding agents is also effective in preserving an equivalently substantial amount of mRNA. In all cases, for the control, the H&E sample, and the rapid fluorescent method, a faint band appears in the $10^5$ dilution lane, illustrating the substantial preservation of RNA accomplished by limiting the total exposure time of the tissue sample to aqueous solutions to a total of 1.3 minutes. Densitometry of the $10^5$ dilution band revealed that as much RNA is preserved in tissue by either rapid H&E staining or rapid immunofluorescent staining as is preserved in tissue never exposed to aqueous solutions.

The level of preservation is markedly superior to the results observed after immunohistochemical labeling according to the method of Fend et al. (*American Journal of Pathology*, 154: 61–66, 1999), which preserves only 1% of the mRNA for β-actin (Kohda et al., *Kidney International*, 57: 321–331, 2000). The rapid fluorescent specific binding agent labeling methods thus preserve a greater percentage of biological molecules, for example more than about 5%, such as 10%, or even more than about 20%. In some embodiments 50%, 70%, 80%, 95%, or even up to 100% of the biological molecules are preserved.

Having previously demonstrated that the fluorescent labeling/low-light level detection/microdissection methods enable direct visualization and isolation of specific cells and tissue structures from a tissue samples that are rapidly stained with fluorescent specific binding agents and here demonstrating the substantial preservation of RNA that accompanies the methods of the present disclosure, it will be evident that the disclosed methods are useful for studies of cell-level genomics, including measurement of mRNA expression.

TABLE 1

Sequences of oligonucleotide primers

| Gene | GenBank Identifier | Oligonucleotide sequence | Location Bp | Product size bp |
|---|---|---|---|---|
| Mouse MDH | (M29462) | | | |
| 5' sense | | GGTCATTGTTGTGGGAAACC | (456–475) | 431 |
| 3' sense | | TCGACACGAACTCTCCCTCT | (867–886) | |
| Mouse AQP2 | (AF020519) | | | |
| 5' sense | | ATGTGGGAACTCCGGTCCATA | (1–21) | 477 |
| 3' sense | | GCTACCCAGGTTGTCACTGC | (458–477) | |
| Mouse THP | (L33406) | | | |
| 5' sense | | TCAGCCTGAAGACCTCCCTA | (1430–1449) | 230 |
| 3' sense | | TGTGGCATAGCAGTTGGTCA | (1640–1659) | |
| Mouse BAT | (D88533) | | | |
| 5' sense | | ACGTCTTCCTCGTGGTTCTG | (1814–1833) | 315 |
| 3' sense | | GGCATCTCTTAGGGAGCTT | (2110–2128) | |

Genes are identified by GenBank abbreviations. Abbreviations: bp, base pair; MDH, malate dehydrogenate; AQP2, aquaporin-2; THP, Tamm-Horsfall protein; BAT, dibasic and neutral amino acid transporter.

Example 6
Laser Assisted Microdissection of the Fetal Rat Brain Based Upon Differential Expression of the NMDA Receptor Subunits N-methyl-D-aspartate (NMDA) receptors constitute cation channels of the central nervous system that are gated by the excitatory neurotransmitter L-glutamate. Activation of NMDA receptors is essential for inducing long-term potentiation, a form of activity-dependent synaptic plasticity that is implicated in the learning process in animal behavioral models. NMDA-receptor channel activities also play a role in neuronal development.

In vitro reconstitution experiments with cloned NMDA have revealed that the physiological and pharmacological properties of the heteromeric NMDA receptor appear to be imparted by the particular type 2 subunit. (See for example, *Mol. Pharmacol*, 45: 540, 1994) Subunits 2A and 2 B are found primarily in the hippocampus and cortex, whereas 2C is found mainly in the cerebellum. This differential expression is utilized to identify and isolate cells in the fetal rat brain that are destined to become part of the mature cerebellum. The cells are microdissected from the labeled cells using a laser assisted microdissection apparatus as modified by Fink et al., *Lab Invest.*, 80: 327–333, 2000.

Fetal rat brain sections 5 μm thick are fixed for 2 minutes in cold ethanol, washed twice, 30 seconds each, with DEPC-treated PBS pH 7.6 and then treated with a pre-mixed (10 minutes) solution of diluted anti-rat NMDA receptor, subunit 2C, rabbit IgG fraction (A-6475, Molecular Probes, Eugene, Oreg.) and diluted Alexa Fluor 488 protein G conjugate (P-11065, Molecular Probes, Eugene, Oreg.) for 2 minutes. The mixture has a final concentration of anti-NMDA receptor of 0.04 mg/mL and the protein G conjugate is present at a concentration of 0.2 mg/mL. Subsequent to incubation the fluorescent specific binding agent, the section is washed twice for 15 seconds each with PBS/DEPC, dehydrated and air dried. Slides are viewed with a FITC filter cube and low light level microscopy as described above. A group of cells of the fetal rat tissue labeled by the anti-NMDA/Protein-G mixture are targeted for laser assisted microdissection and removed from the tissue section. A portion of the fetal rat tissue not labeled by the anti-NMDA/Protein-G mixture is also selected and removed from the tissue section.

The microdissected portions are each extracted and then analyzed by two-dimensional polyacrylamide gel electrophoresis to detect differences between the protein products expressed in fetal rat tissue destined to become cerebellum tissue and those expressed in fetal rat tissue destined to become other portions of the mature rat brain.

Example 7
Isolation of Neuromuscular Junctions, Muscle Spindles, and Cutaneous Nerves in the Mouse Peripheral Nervous System Borges and Sidman (*J. Neurosci*, 2: 647–53, 1982) demonstrated that lectins known to bind preferentially to N-acetylglucosamine or mannose sugars are transported axonally to ventral horn and dorsal ganglion neurons. Twelve to 96 hours post-injection into adult mice they demonstrated that these lectins are bound at the injection site to neuromuscular junctions, muscle spindles, and cutaneous nerves. The selective binding of such lectins may be utilized to selectively label nerve structures in a tissue sample.

In order to isolate neuromuscular junctions, muscle spindles, and cutaneous nerves, a mouse is injected with a lectin that binds to cells bearing N-acetylglucosamine or mannose sugars. Ninety-six hours later, the tissue surrounding the injection site is biopsied, frozen and sectioned to 2 μm. The sections are mounted on a slide, washed for 10 seconds with DEPC/PBS and then treated with a 0.5 mg/mL buffered solution of a fluorescent conjugate of lectin HPA from Helix pomatia (L-11271, Molecular Probes, Eugene, Oreg.) for 1 minute. The sections are washed twice for 5 seconds each with DEPC/PBS, dehydrated and dried. Sections are viewed with a FITC filter cube and low light level video microscopy as described in Example 1. Specific portions of the histologic section corresponding to the location of the specifically labeled tissue structures are then microdissected from the tissue sections.

Example 8
Fluorescent Specific Binding Agents

Fluorescent specific binding agents are fluorescent (intrinsically or after conjugation with a fluorescent moiety) molecules that preferentially bind in a specific manner to other molecules that are present inside or on the surface of particular types of cells or tissue structures. Once bound, fluorescent specific binding agents serve to highlight particular cells or tissue structures within a tissue sample and enable their identification. Fluorescent specific binding agents include fluorescent antibodies, fluorescent lectins, and other fluorescent proteins, such as proteins A and G, which recognize and bind selectively to other molecules that are associated with particular types of cells or tissue structures.

The choice of fluorescent specific binding agent is one factor in successful application of microdissection methods. For example, in injured kidney tissue, expression of the Tamm-Horsfall protein is known to decrease following renal ischemia; detection of ischemic thick ascending limbs with fluorescent antibodies against the Tamm-Horsfall protein is difficult. However, the amount of Na—K-2Cl co-transporter does not decrease following ischemia (see Fernandez-Llama et al., *J. Am. Soc. Mephrol.*, 10: 1658–1668, 1999 and Kwon et al., *Am. J. Physiol. Renal Physiol.*, 278: F925–F939, 2000). Thus, fluorescent antibodies directed toward the co-transporter protein are useful for identifying ischemic thick ascending limbs. In general, fluorescent specific binding agents may be chosen so that they bind preferentially to the specific cells or tissue structures that are to be isolated by microdissection. Alternatively, it is possible to choose fluorescent specific binding agents so that the desired cells or tissue structures are the only parts of a tissue sample that are not labeled by the fluorescent specific binding agent because, for example, they fail to express a particular protein antigen.

Fluorescent specific binding agents include fluorescent primary antibodies.

Fluorescent primary antibodies that specifically bind to certain antigenic molecules, such as particular proteins or carbohydrates, are available commercially from many sources including Molecular Probes, Inc. (Eugene, Oreg.) and BAbCo (Richmond Calif.). Commercially available antibodies may also be converted to fluorescent conjugates using reactive fluorescent moieties. Fluorescent moieties that may be conjugated to antibodies include ALEXA dyes (Molecular Probes, Eugene Oreg.), fluoresceins, coumarins, rhodamines, phycobiliproteins, Texas Red, phycoerythrins, and pyridyloxazoles, among others. Currently unavailable monoclonal or polyclonal antibodies against a particular antigen, such as a particular protein, may also be produced using methods well known in the art and subsequently conjugated with a fluorescent moiety For example, an antigen specific to a type of cell within a tissue sample may be produced by injecting the antigen into a host animal, repeatedly, over a period of time. If the desired antigen is a small molecule, it may be conjugated to a large protein, such as Bovine Serum Albumin, before it is administered to the host animal. Suitable host animals for this purpose include mammals such as rabbits, horses, goats, guinea pigs, rats, cows, sheep, etc. The serum is collected from the host animal and the antibody is precipitated with a neutral salt solution and purified by dialysis and column chromatography. The resulting polyclonal antibody, is actually a multiplicity of antibodies that selectively complex with the antigen. Alternatively, lymphocytes are isolated from the host animal and fused to myeloma cells. The resulting hybridoma cells are selected based on their production of antibodies toward the antigen, cloned, and cultured. The antibody is then isolated from the culture medium. The antibody isolated from the clones of a particular hybridoma is termed a monoclonal antibody. Finally, either a monoclonal or polyclonal antibody preparation is treated with a reactive fluorescent moiety to produce fluorescent conjugates of antibodies, which may be purified, for example, by size exclusion chromatography. Commercial kits for producing fluorescent conjugates of antibodies and other proteins are available (For example, the Alexa Fluor Protein Labeling Kit from Molecular Probes, Inc., Eugene, Oreg.).

Fluorescent specific binding agents also include mixtures of primary and secondary antibodies; one or both of which are fluorescent. If the primary antibody is not fluorescent, the secondary antibody is fluorescent. The use of fluorescent secondary antibodies toward particular types of antibody molecules, such as mouse IgG, allow fluorescent detection of any primary antibody of the same type as recognized by the secondary antibody. The fluorescence signal can be amplified by employing combinations of primary and secondary antibodies where both the primary and the secondary antibodies are conjugated to a fluorescent moiety.

Fluorescent specific binding agents include lectins, proteins that bind specifically to certain configurations of sugar molecules. When conjugated with fluorescent moieties, such as those mentioned above, lectins may be utilized to delineate cells and tissues based upon the presence of particular proteoglycans, glycoproteins, and glycolipids on their surface.

Fluorescent specific binding agents also include fluorescent conjugates of proteins A and protein G. Conjugates of protein A and protein G, bacterial proteins that bind with high affinity to the Fc portion of various classes and subclasses of immunoglobulins from a number of species, may be utilized in place of secondary antibodies. Such conjugates are available from Molecular Probes, Inc. (Eugene, Oreg.). Again, for amplification of the fluorescence signal, the primary antibody may also bear a fluorescent moiety.

It is also possible to utilize mixtures of fluorescent specific binding agents simultaneously to identify particular cells or tissue structures. The fluorescent specific binding agents may all fluoresce at the same wavelength or alternatively, at several wavelengths. For example, it may be desirable to utilize a mixture of fluorescent specific binding agents that all fluoresce at the same wavelength to label all the cells except those that are to be isolated by microdissection. Alternatively, the mixture of fluorescent specific binding agents could be a mixture of agents that fluoresce at different wavelengths. Such mixtures might, for example, allow several different types of cells to be simultaneously microdissected or allow selection of tissue portions for microdissection based upon specific combinations of labeling by the fluorescent specific binding agents.

Monoclonal antibodies and antibodies that give strong signals with conventional immunofluorescence protocols work best, with the least background fluorescence. Fluorescent antibodies and other fluorescent specific binding agents that require long incubation times may not be appropriate for the rapid labeling methods. However, increasing the sensitivity of the low light level detection system (e.g., to the single fluorescing molecule level with a GenIV image intensifier coupled to a sensitive ICCD camera), signal averaging (image processing), and using image enhancement (Example 1) may allow use of even weakly binding antibodies. Alternatively, if some loss of biological molecules can be tolerated, aqueous exposure can be extended, for example up to between 3 and 5 minutes. For instance, 3 minutes of exposure to fluorescent specific binding agents and 2 minutes of washing, combined with low light level detection and image enhancement, may allow cells and tissue structures labeled with weakly binding fluorescent specific binding agents to be identified above the background fluorescence.

Example 9

Genomics and Proteomics

The disclosure also includes methods that combine rapid specific fluorescent labeling and microdissection of pure populations of cells and tissue structures with other technologies, such as high-throughput genomics, to identify molecular characteristics, such as structural changes in genes or proteins, copy number or expression alterations of genes, with disease prognosis or therapy outcome, to identify novel targets for gene prevention, early diagnosis, disease classification, or prognosis, and to identify therapeutic agents. Such high-throughput technologies include cDNA and genomic sequencing, serial analysis of gene expression (SAGE), representational difference analysis (RDA), differential display and related PCR-based technologies, hybridization-based sequencing, subtractive cDNA or genomic hybridizations, cDNA arrays, CGH arrays, electrophoretic, mass spectrometric, or other separation and identification methods (including SELDI fingerprinting) for DNA or proteins, yeast two-hybrid technology or related techniques of molecular biology.

A particular example of an important high throughput proteomic technique that may be combined with the methods of the present disclosure is SELDI protein fingerprinting. SELDI analysis or proteins from samples microdissected according to the disclosure may be used, for example, to assess changes in protein expression occurring during tumor progression. SELDI analysis of pure populations of cells and tissue structures obtained by rapid fluorescent specific binding agent and low-light level detection microdissection advantageously will provide a more complete picture of cell level proteomics that includes proteins with short half-lives in aqueous solutions. Such information will aid in the elucidation of the fundamental mechanisms underlying carcinogenesis and identification of markers that may be utilized for diagnostic purposes. Such analyses are not however restricted to a particular disease state and may also be utilized to elucidate mechanisms of tissue damage and repair in response to injury, chemical, physical, or otherwise.

Pure cell and tissue structure samples microdissected according to the methods of this disclosure may also be used in combination with array techniques and can provide information about the frequency of a multitude of genetic alterations or gene expression patterns (including normal gene expression patterns) in a variety of tissue types (such as different types of tumors), and in tissue of a particular histological type (such as a tumor of a specific type, such as intraductal breast cancer), as well as the tissue distribution of molecular markers tested.

Differential gene expression, which can be detected by varying levels of proteins or RNA detected by this microdissection technique, can then be used for diagnostic or therapeutic purposes. For example, overexpression or underexpression of particular proteins can be associated with particularly benign or malignant tumors, to provide prognostic information about the likely clinical course of a tumor (and decide whether aggressive chemotherapy must be undertaken). Similarly, information about differential protein expression in particular types of disease (such as tumors of a particular type) can be used to target treatment. Hence if upregulation of a protein is found in a particular type of tumor cell, therapies aimed at disruption of that upregulation can be administered. The use of the microdissection techniques disclosed herein, for both diagnostic and therapeutic purposes, is therefore included.

In view of the many possible embodiments to which the principles of our invention may be applied, it should be recognized that the illustrated embodiments are only specific examples and should not be taken as a limitation on the scope of the invention. Rather, the scope of the invention is defined by the following claims. We therefore claim as our invention all that comes within the scope and spirit of these claims.

We claim:

1. A method for microdissecting a tissue sample, comprising:

pre-mixing a primary antibody and a secondary antibody, at least one of which is fluorescently labeled, to form a fluorescent specific binding agent;

contacting the tissue sample with the fluorescent specific binding agent to provide selectively labeled cells in the tissue sample;

identifying the selectively labeled cells in the sample by detecting fluorescence of the selectively labeled cells in the tissue sample; and microdissecting the selectively labeled target cells from the tissue.

2. A method for microdissecting a tissue sample, comprising:

pre-mixing a primary antibody and a secondary antibody, at least one of which is fluorescent, to generate a fluorescent specific binding agent;

contacting the tissue sample with the fluorescent specific binding agent to provide selectively labeled cells in the tissue sample;

identifying the selectively labeled cells in the sample by detecting fluorescence of the selectively labeled cells in the tissue sample; and microdissecting the selectively labeled target cells from the tissue;

wherein pre-mixing the primary antibody and the secondary antibody occurs prior to exposing the tissue to the fluorescent specific binding agent in order to reduce a time of exposure of the tissue to the fluorescent specific binding agent.

3. A method for microdissecting tissue, comprising:

labeling a sample of tissue using a method comprising:
      premixing a primary antibody and a secondary antibody, at least one of which is fluorescently labeled, to form a fluorescent specific binding agent, prior to exposing the tissue to the fluorescent specific binding agent;
      contacting the tissue with the fluorescent specific binding agent at a concentration to provide selectively labeled cells against which the fluorescent specific binding agent is directed in less than about five minutes;
      wherein the biological molecule in the tissue is preserved after the tissue is contacted with the fluorescent specific binding agent, by labeling the cells in less than five minutes;

identifying the selectively labeled cells in the sample by detecting fluorescence of the selectively labeled cells in the tissue; and microdissecting the selectively labeled cells from the tissue.

* * * * *